(12) United States Patent
Wong (10) Patent No.: US 11,389,647 B2
(45) Date of Patent: Jul. 19, 2022

(54) NEUROLOGICAL STIMULATION LEAD ANCHORS AND ASSOCIATED TOOLS, AND METHODS

(71) Applicant: Nevro Corp., Redwood City, CA (US)

(72) Inventor: Mark Steven Wong, Redwood City, CA (US)

(73) Assignee: Nevro Corp., Redwood City, CA (US)

( * ) Notice: Subject to any disclaimer, the term of this patent is extended or adjusted under 35 U.S.C. 154(b) by 175 days.

(21) Appl. No.: 16/780,502

(22) Filed: Feb. 3, 2020

(65) Prior Publication Data

US 2021/0236811 A1  Aug. 5, 2021

(51) Int. Cl.
*A61N 1/05* (2006.01)
*A61N 1/375* (2006.01)

(52) U.S. Cl.
CPC ....... *A61N 1/0558* (2013.01); *A61N 1/37518* (2017.08); *A61N 2001/058* (2013.01)

(58) Field of Classification Search
CPC .............. A61N 1/0558; A61N 1/37518; A61N 2001/058; A61N 2001/0582
See application file for complete search history.

(56) References Cited

U.S. PATENT DOCUMENTS

| | | | | |
|---|---|---|---|---|
| 942,517 A | * | 12/1909 | Reynolds | A44C 7/003 24/707.4 |
| 947,111 A | * | 1/1910 | Lorentz | F16G 11/00 24/129 R |
| 4,270,491 A | * | 6/1981 | Cox | A01K 27/005 119/793 |
| 4,573,448 A | | 3/1986 | Kambin | |
| 5,070,605 A | | 12/1991 | Daglow | |
| 5,730,628 A | | 3/1998 | Hawkins | |
| 5,766,042 A | | 6/1998 | Ries et al. | |
| 5,843,146 A | | 12/1998 | Cross, Jr. | |
| 6,042,432 A | | 3/2000 | Hashizawa | |
| 6,138,475 A | * | 10/2000 | Kohl | A44C 7/003 63/3.1 |

(Continued)

FOREIGN PATENT DOCUMENTS

| | | |
|---|---|---|
| EP | 2086630 | 11/2010 |
| EP | 1477203 | 9/2015 |

(Continued)

OTHER PUBLICATIONS

International Search Report and Written Opinion for International Patent Application No. PCT/US2021/015279, Applicant: Nevro Corp., dated May 12, 2021, 8 pages.

(Continued)

*Primary Examiner* — Eugene T Wu
(74) *Attorney, Agent, or Firm* — Perkins Coie LLP (57) ABSTRACT

A lead anchor comprising a longitudinally extending anchor body and a retainer. The longitudinally extending anchor body having a lumen positioned to receive a spinal cord lead therethrough and having a retainer pocket intersecting the lumen. The retainer is positioned in the retainer pocket. The retainer comprises a first grip member having at least one first aperture, a second grip member having at least one second aperture, and at least one U-shaped resilient portion connecting the first and second grip members.

8 Claims, 11 Drawing Sheets

(56) References Cited

U.S. PATENT DOCUMENTS

| | | | |
|---|---|---|---|
| 6,305,053 B1* | 10/2001 | Galbreath | F16G 11/101 24/129 R |
| 6,451,030 B2 | 9/2002 | Li et al. | |
| 6,473,654 B1 | 10/2002 | Chinn | |
| 6,540,568 B2 | 4/2003 | Miyazaki | |
| 6,971,393 B1 | 12/2005 | Marno | |
| 7,184,841 B1 | 2/2007 | Bodner et al. | |
| 7,200,446 B2 | 4/2007 | Borkan | |
| 7,853,321 B2 | 12/2010 | Jaax et al. | |
| 8,019,443 B2 | 9/2011 | Schleicher et al. | |
| 8,140,172 B1 | 3/2012 | Jones et al. | |
| 8,200,343 B2 | 6/2012 | Gerber et al. | |
| 8,204,569 B2 | 6/2012 | Gerber et al. | |
| 8,229,573 B2 | 7/2012 | Chen et al. | |
| 8,249,720 B2 | 8/2012 | Verzal et al. | |
| 8,301,268 B1 | 10/2012 | Jones et al. | |
| 8,412,349 B2 | 4/2013 | Barker | |
| 8,467,883 B2 | 6/2013 | Chen | |
| 8,483,845 B2 | 7/2013 | Sage | |
| 8,644,954 B2 | 2/2014 | Jaax et al. | |
| 8,727,817 B2* | 5/2014 | D'Hiver | A61N 1/05 439/789 |
| 8,761,902 B2 | 7/2014 | Kulle | |
| 9,026,226 B2 | 5/2015 | Gerber et al. | |
| 9,089,672 B2 | 7/2015 | Hendriksen et al. | |
| 9,138,574 B2 | 9/2015 | Kern et al. | |
| 9,265,935 B2 | 2/2016 | Thacker | |
| 9,409,010 B2 | 8/2016 | Farhat et al. | |
| 9,504,839 B2 | 11/2016 | Leven | |
| 9,510,818 B2 | 12/2016 | Lee | |
| 9,517,332 B2 | 12/2016 | Olson et al. | |
| 9,517,334 B2 | 12/2016 | Barner et al. | |
| 9,687,649 B2 | 1/2017 | Thacker et al. | |
| 9,889,293 B2 | 2/2018 | Siegel et al. | |
| 9,987,482 B2 | 6/2018 | Nageri et al. | |
| 10,016,604 B2 | 7/2018 | Biele et al. | |
| 10,092,744 B2 | 10/2018 | Sommer et al. | |
| 10,105,536 B2 | 10/2018 | Orts et al. | |
| 2001/0000800 A1 | 5/2001 | Partridge et al. | |
| 2002/0072787 A1 | 6/2002 | Partridge et al. | |
| 2003/0114895 A1 | 6/2003 | Gordon et al. | |
| 2005/0021119 A1 | 1/2005 | Sage | |
| 2006/0127158 A1 | 6/2006 | Olson et al. | |
| 2007/0044278 A1* | 3/2007 | Kinebuchi | F16G 11/101 24/115 G |
| 2007/0255295 A1 | 11/2007 | Starkbaum et al. | |
| 2008/0103573 A1 | 5/2008 | Gerber | |
| 2008/0103576 A1 | 5/2008 | Gerber | |
| 2008/0183221 A1 | 7/2008 | Burdulis | |
| 2009/0048638 A1 | 2/2009 | Rey et al. | |
| 2009/0259280 A1 | 10/2009 | Wilkin et al. | |
| 2011/0004281 A1 | 1/2011 | Jones | |
| 2011/0022141 A1* | 1/2011 | Chen | A61N 1/0558 607/117 |
| 2011/0166582 A1 | 7/2011 | Syed et al. | |
| 2013/0138191 A1 | 5/2013 | Jones | |
| 2013/0245739 A1 | 9/2013 | Arber | |
| 2013/0296957 A1 | 11/2013 | Tronnes | |
| 2014/0081362 A1 | 3/2014 | Wicklund | |
| 2014/0155973 A1 | 6/2014 | Grigsby et al. | |
| 2016/0346553 A1 | 12/2016 | Black | |
| 2017/0151428 A1 | 6/2017 | Schleicher et al. | |
| 2017/0151432 A1 | 6/2017 | Christopherson et al. | |
| 2017/0189676 A1 | 7/2017 | Bentley et al. | |
| 2017/0252032 A1 | 9/2017 | Hiorth et al. | |
| 2018/0099147 A1 | 4/2018 | Kane et al. | |
| 2018/0296827 A1 | 10/2018 | Pianca et al. | |
| 2018/0311494 A1 | 11/2018 | Wang et al. | |
| 2019/0001122 A1 | 1/2019 | Ganty et al. | |
| 2019/0105503 A1 | 4/2019 | Leven | |
| 2019/0308010 A1 | 10/2019 | Sunken et al. | |

FOREIGN PATENT DOCUMENTS

| | | |
|---|---|---|
| EP | 1334745 | 5/2017 |
| EP | 2539016 | 11/2017 |
| EP | 2731671 | 4/2019 |
| WO | WO-2014209814 | 12/2014 |

OTHER PUBLICATIONS

Kulkarni et al., "A two-layered forward model of tissue for electrical; impedance tomography," Physiol Meas., 30(6); pp. 1-24, Jun. 2009.

* cited by examiner

NEUROLOGICAL STIMULATION LEAD ANCHORS AND ASSOCIATED TOOLS, AND METHODS

TECHNICAL FIELD

The present disclosure is directed generally to lead anchors for positioning and securing neurological stimulation system leads and/or other signal delivery elements. More specifically, the disclosure is directed to lead anchors for positioning and securing spinal cord stimulation and modulation leads.

BACKGROUND

Neurological stimulators have been developed to treat pain, movement disorders, functional disorders, spasticity, cancer, cardiac disorders, and various other medical conditions. Implantable neurological stimulation systems generally have an implantable signal generator and one or more leads that deliver electrical pulses to neurological or muscle tissue. For example, several neurological stimulation systems have cylindrical leads that include a lead body with a circular cross-sectional shape and one or more conductive rings (e.g., contacts) spaced apart from each other at the distal end of the lead body. The conductive rings can operate as individual electrodes and, in many cases, the leads are implanted percutaneously through a large needle inserted into the epidural space, with or without the assistance of a stylet.

Once implanted, the signal generator applies electrical pulses to the electrodes, which in turn modify the function of the patient's nervous system, such as by altering the patient's responsiveness to sensory stimuli and/or altering the patient's motor-circuit output. In pain treatment, the signal generator applies electrical pulses to the electrodes, which in turn can mask or otherwise alter the patient's sensation of pain.

It is important to accurately position and anchor the leads in order to provide effective therapy. For example, in both traditional low frequency spinal cord stimulation (SCS) and high frequency spinal cord modulation therapy, one or more leads are positioned along a patient's spine to provide therapy to a specific vertebral area. Existing lead anchors can negatively impact lead performance and/or reliability when they allow the lead body to slide or otherwise change position relative to a treatment area. The movement of the lead body relative to the lead anchor can reduce the accuracy with which the stimulation is provided, thus limiting the effectiveness of the therapy. In some cases, the leads must be securely fixed but still be repositionable if a practitioner determines that a different position would provide more effective therapy. As a result, there exists a need for a lead retention mechanism, such as a lead anchor, that mitigates lead movement while providing the ability to subsequently reposition the lead.

BRIEF DESCRIPTION OF THE DRAWINGS

Embodiments of representative lead anchors, tools, and methods described herein may be better understood by referring to the following Detailed Description in conjunction with the accompanying drawings, in which like reference numerals indicate identical or functionally similar elements.

The headings provided herein are for convenience only and do not necessarily affect the scope of the embodiments. Further, the drawings have not necessarily been drawn to scale. For example, the dimensions of some of the elements in the Figures may be expanded or reduced to help improve the understanding of the embodiments. Moreover, while the disclosed technology is amenable to various modifications and alternative forms, specific embodiments have been shown by way of example in the drawings and are described in detail below. The intention, however, is not to unnecessarily limit the described embodiments. On the contrary, the embodiments are intended to cover all suitable modifications, combinations, equivalents, and/or alternatives of the technology falling within the scope of this disclosure.

DETAILED DESCRIPTION

Overview

The present technology is directed generally to lead anchors, lead anchor actuation tools, and methods of anchoring a lead to a patient that mitigate lead movement while providing the ability to subsequently reposition the lead. In general, the lead anchors and methods are for use with neurological stimulation systems, such as spinal cord modulation systems. In particular embodiments, the lead anchor can include a retainer that releasably attaches a lead to a lead anchor. The lead anchor can in turn be attached to a patient with sutures. Specific details of several embodiments of the technology are described below with reference to representative anchors and tools to provide a thorough understanding of these embodiments, but other embodiments can have other arrangements. Several details describing structures or processes that are well-known and often associated with lead anchors and associated devices but that may unnecessarily obscure some significant aspects of the disclosure are not set forth in the following description for purposes of clarity. Moreover, although the following disclosure sets forth several embodiments of different aspects of the technology, several other embodiments of the technology can have different configurations or different components than those described in this section. As such, the technology may have other embodiments with additional elements and/or without several of the elements described below with reference to FIGS. 1A-11B.

General Description

Figure 1A:
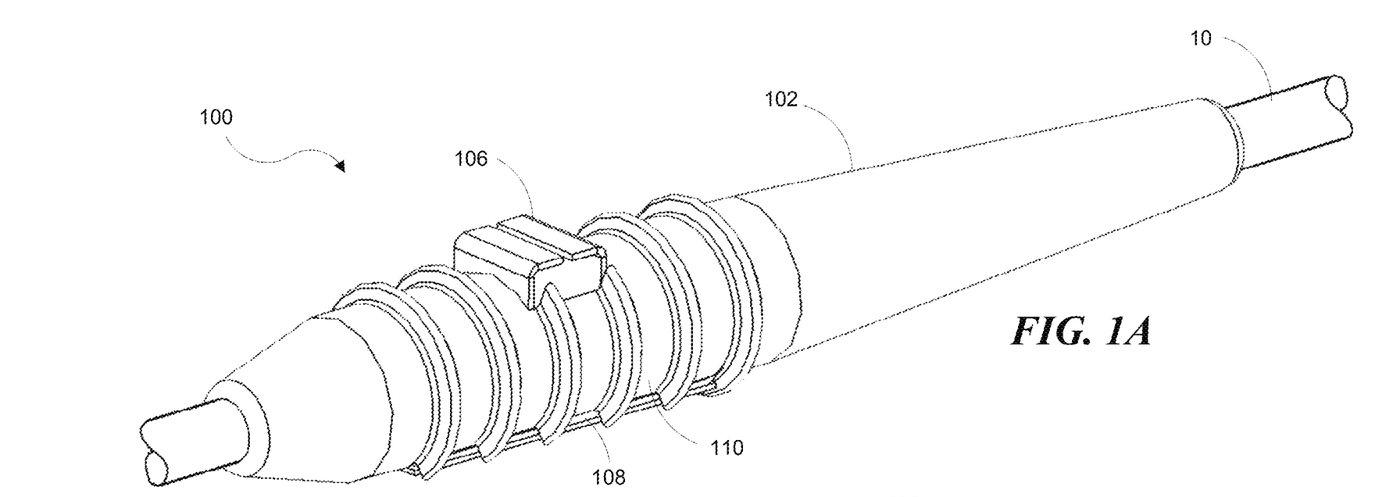
FIG. 1A is an isometric view of a lead anchor according to representative embodiments of the present technology.
Figure 1B:
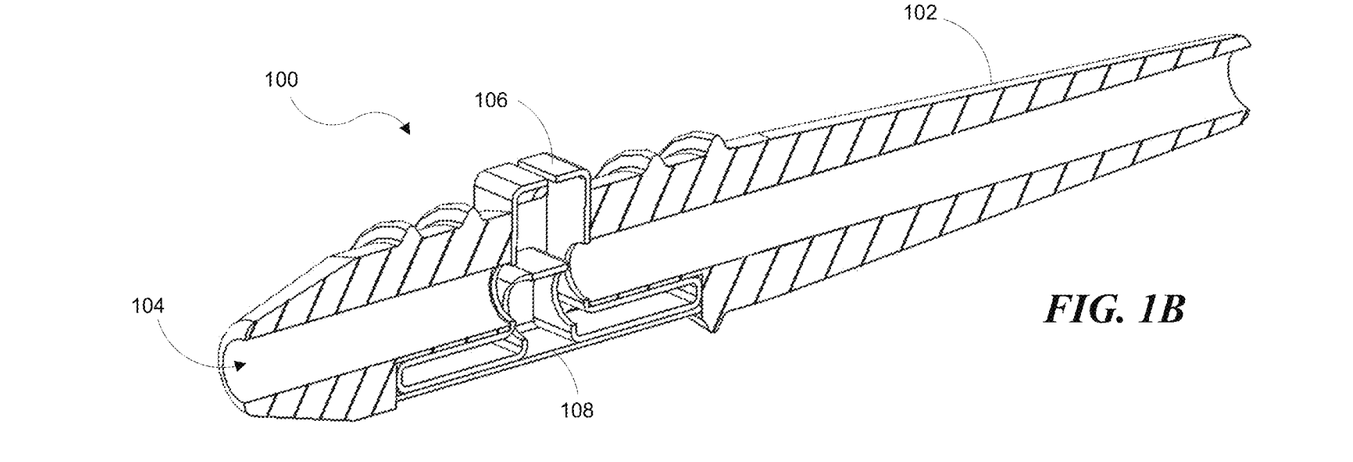
FIG. 1B is an isometric cross-sectional view of the representative lead anchor shown in FIG. 1A.

FIGS. 1A and 1B illustrate a lead anchor 100 according to representative embodiments of the present technology. The lead anchor 100 releasably engages or grips a lead 10 (e.g., an electrical stimulation or modulation lead) and anchors the lead 10 relative to a patient's tissue. The lead anchor 100 can include a longitudinally extending anchor body 102 having a longitudinally extending aperture or lumen 104 that receives the lead 10. A retainer 106 is positioned in the anchor body 102 and is operable to grip at least a portion of the lead 10 extending through the anchor body 102. The lead 10 is accordingly retained in position relative to the lead anchor 100 by the retainer 106. The anchor body 102 can include multiple circumferential suture grooves 110. The grooves 110 act to keep sutures, which are used to attach the anchor 100 to the patient, properly aligned around the anchor body 102. Thus, the lead anchor 100 may be attached to a patient by suturing around the anchor body 102 with the suture threads captured in the grooves 110. In some embodiments, the lead anchor 100 can include a retainer cover 108 to enclose the retainer 106 in the anchor body 102. The anchor body 102 and the retainer cover 108 can be formed from a flexible material, such as a biocompatible material. An example of a suitable flexible biocompatible material is silicone rubber.

The lumen 104 can be sized to provide clearance between the inner surface of the anchor body 102 and the outer surface of the lead 10 such that the lead 10 may be moved into position relative to the lead anchor 100 as long as the retainer 106 is disengaged from the lead 10 (described further below with reference to FIGS. 2A-2C). The clearance between the lumen 104 and lead 10 may be, for example and without limitation, in the range of from about 0.001 inch to about 0.005 inch.

Figure 2A:
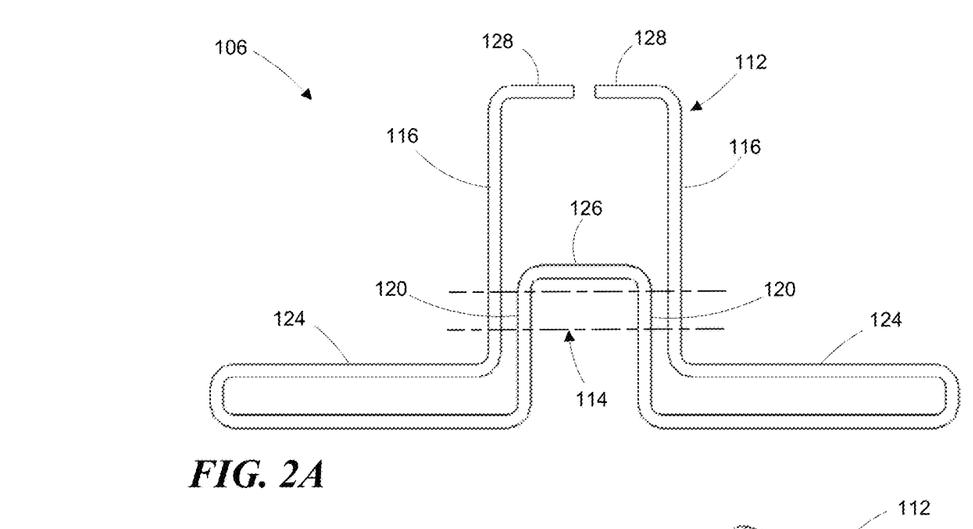
FIG. 2A is a side view in elevation of a representative spring clip shown in FIGS. 1A and 1B.
Figure 2B:
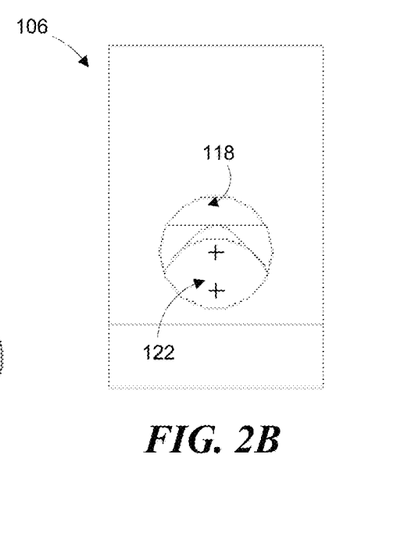
FIG. 2B is an end view of the representative spring clip shown in FIG. 2A.
Figure 2C:
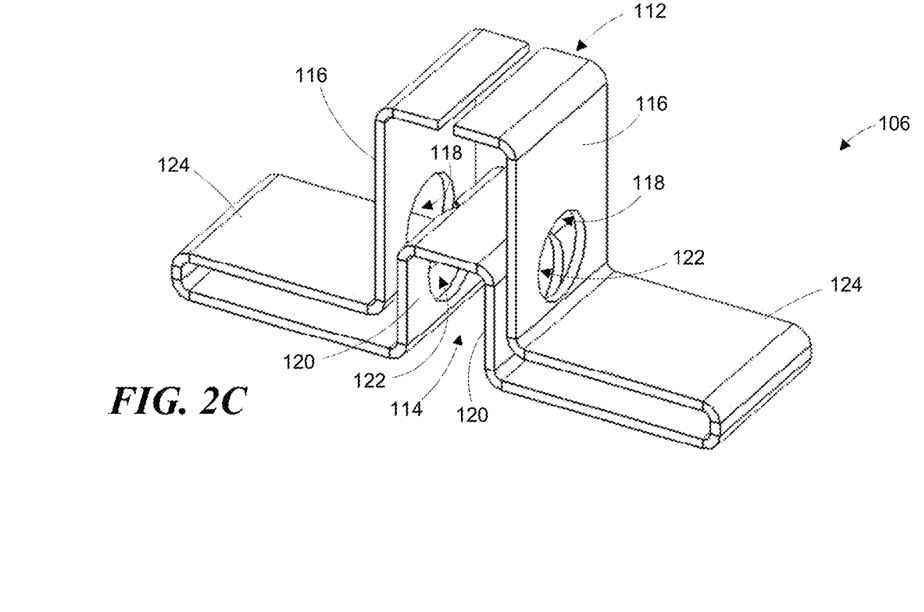
FIG. 2C is an isometric view of the representative spring clip shown in FIGS. 2A and 2B.

As shown in FIGS. 2A-2C, the retainer 106 can include an outer or first grip member 112 and an inner or second grip member 114. The first grip member 112 can comprise a pair of opposed first wall portions 116 and a pair of generally coaxial first apertures 118, each formed through a corresponding one of the pair of opposed first wall portions 116. As used herein, the terms "generally" and "approximately" refer to values within 10% of the stated value, unless noted otherwise. Similarly, the second grip member 114 can comprise a pair of opposed second wall portions 120 and a pair of generally coaxial second apertures 122, each formed through a corresponding one of the pair of opposed second wall portions 120. In the depicted embodiment, the second wall portions 120 can be connected with a transverse portion 126. The second grip member 114 is positioned between the pair of opposed first wall portions 116. A pair of U-shaped flat resilient portions, such as spring portions 124 are positioned on opposite sides of retainer 106, each connecting corresponding first and second wall portions 116 and 120. The term U-shaped is used herein to generally refer to spring portions having an angle from about 0 degrees to about 90 degrees between the legs of the spring, including for example V-shaped springs. In some embodiments, the springs can have an angle of approximately 0-30 degrees. The first wall portions 116 can each include a transverse tab 128 each extending toward the other. In some embodiments, the transverse tabs 128 can be joined together (e.g., welded). In some embodiments, the transverse tabs 128 can be configured to leave a gap therebetween, as shown in FIGS. 2A and 2C.

The first apertures 118 are generally aligned with the lumen 104 (see FIG. 1B). However, the second apertures 122 are offset from the first apertures 118 when the U-shaped spring portions 124 are in a relaxed state as shown in FIGS. 2A-2C. The retainer 106 is normally in a relaxed or engaged state in which the lead 10 is pinched between the first apertures and the second apertures. Thus, to insert the lead 10 through the anchor body, or move the lead 10 within the lumen 104, the retainer 106 is actuated (e.g., elastically deformed) to a disengaged state to release the compressive force on the lead 10. To actuate the retainer 106, a user can push the first grip member 112 and the second grip member 114 together to align the first and second apertures 118 and 122, respectively. The user can push the first grip member 112 and the second grip member 114 together by squeezing the retainer 106 or by using a suitable tool, such as the lead anchor tool described below with reference to FIGS. 8, 10A, and 10B.

In some embodiments, the retainer can comprise a continuous strip of material bent (e.g., stamped) into the configuration described herein. For example, the retainer 106 can comprise a material providing a resilient or spring-like behavior. Accordingly, the retainer 106 may be comprised of a metal, such as for example and without limitation, titanium, Elgiloy®, spring steel, or the like. In some embodiments, the retainer 106 can comprise 0.0075 inch thick Elgiloy® material. The retainer 106 may also be formed (e.g., machined, molded, or thermoformed) from resilient plastics, such as, for example and without limitation, ABS, Nylon, Delrin, UHMW polyethylene, and the like. In the depicted embodiment, the various retainer portions are oriented at right angles and/or parallel to each other. For example, the U-shaped spring portions 124 are generally orthogonal to the wall portions 116 and 120, and the first wall portions 116 are generally parallel to the second wall portions 120.

Although the retainer 106 is shown and described as having a pair of first wall portions 116, a pair of second wall portions 120, and a pair of U-shaped spring portions 124 symmetrically arranged, in some embodiments, a retainer can have one first wall portion and one second wall portion connected by a single U-shaped spring portion, for example.

Figure 3:
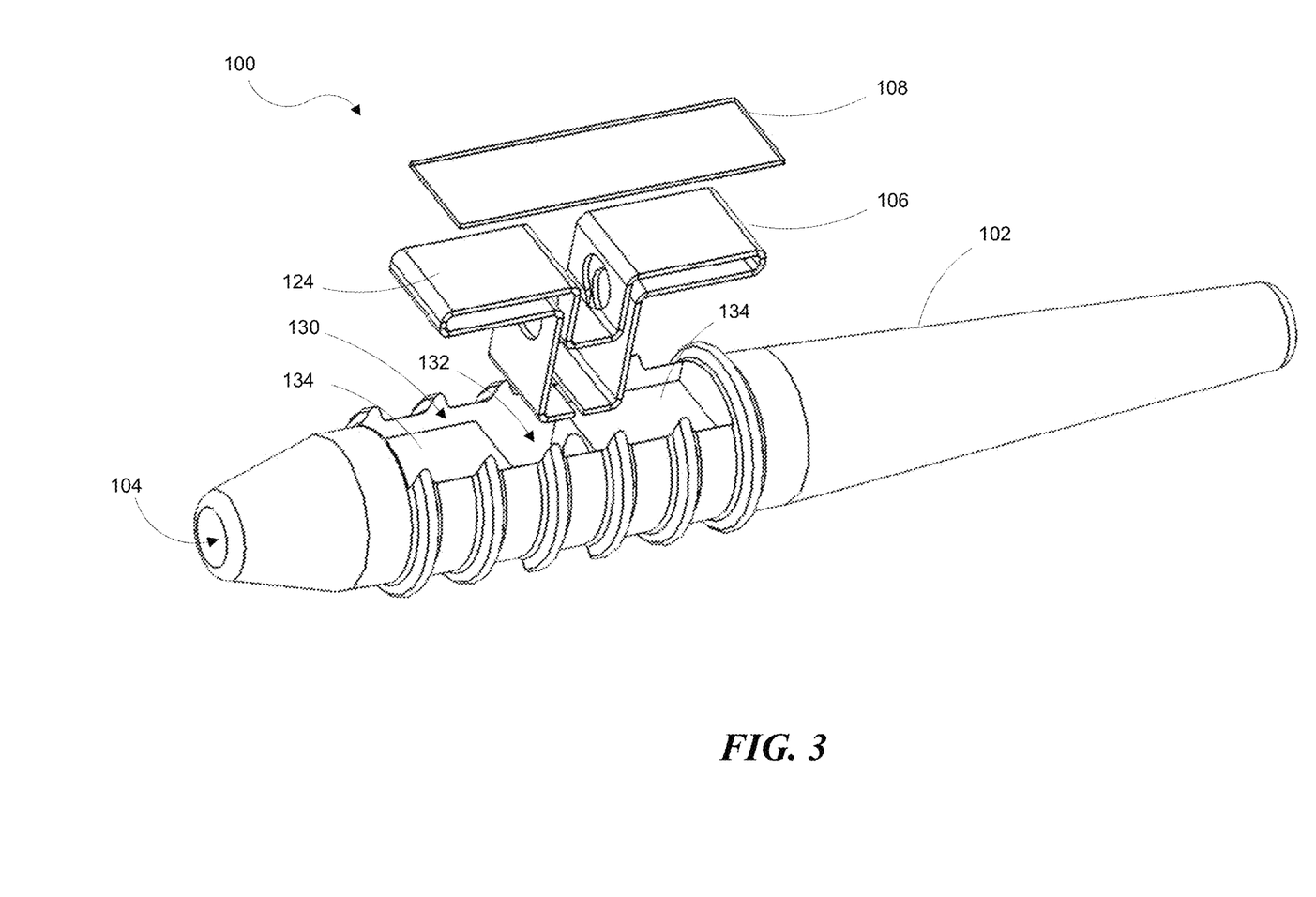
FIG. 3 is an exploded isometric view of the representative lead anchor shown in FIGS. 1A and 1B.

As shown in FIG. 3, the anchor body 102 can include a retainer pocket 130 positioned to receive the retainer 106. The retainer pocket 130 includes a central region 132 extending at least part-way through the anchor body 102 to intersect the lumen 104. The retainer pocket 130 also includes a pair of lateral ledge regions 134, each at least partially containing a corresponding one of the U-shaped spring portions 124. In some embodiments, the retainer 106 is glued into the retainer pocket 130. For example, each U-shaped spring portion 124 can be glued to a corresponding ledge 134. The retainer cover 108 can be glued to the U-shaped spring portions 124 and/or the perimeter of the retainer pocket 130, for example.

Figure 4A:
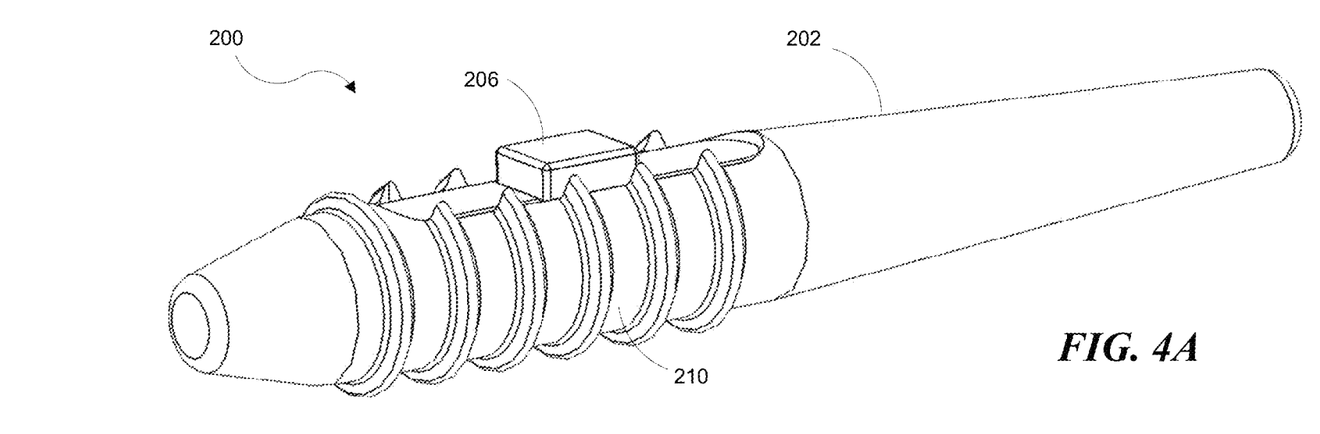
FIG. 4A is an isometric view of a lead anchor according to further representative embodiments of the present technology.
Figure 4B:
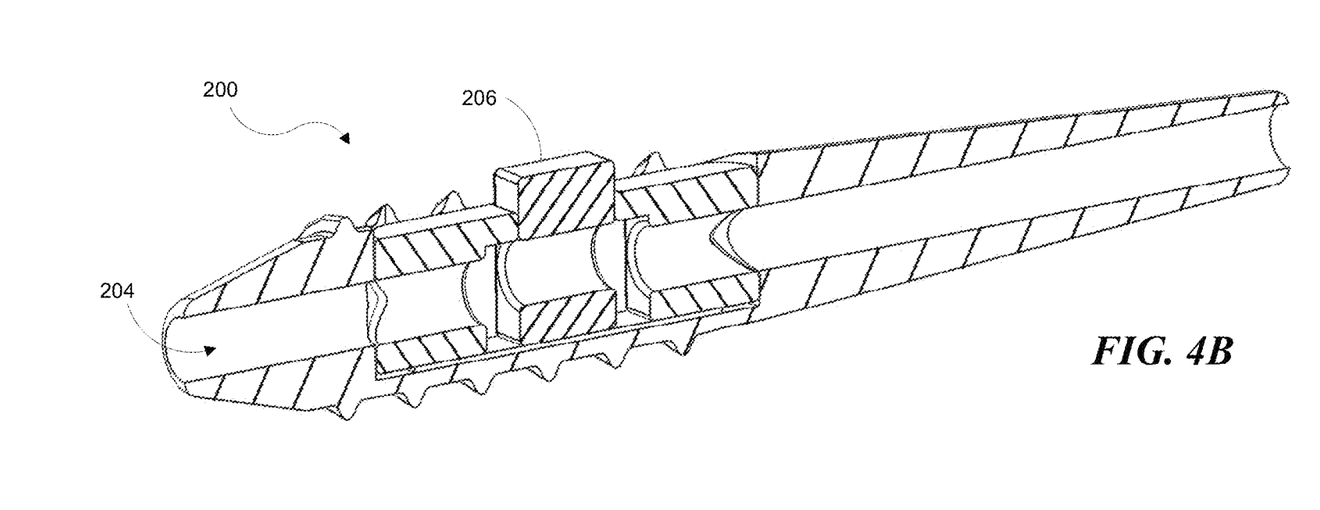
FIG. 4B is an isometric cross-sectional view of the representative lead anchor shown in FIG. 4A.

FIGS. 4A and 4B illustrate a lead anchor 200 according to further representative embodiments of the present technology. The lead anchor 200 releasably carries a lead (such as the lead 10, shown in FIG. 1A) and anchors the lead relative to a patient's tissue. Accordingly, the lead anchor 200 can include a longitudinally extending anchor body 202 having a longitudinally extending aperture or lumen 204 that receives the lead. A retainer 206 is positioned in the anchor body 202 and is operable to grip at least a portion of the lead extending through the anchor body 202. The anchor body 202 can include multiple circumferential suture grooves 210 to facilitate attaching the anchor 200 to a patient.

Figure 5:
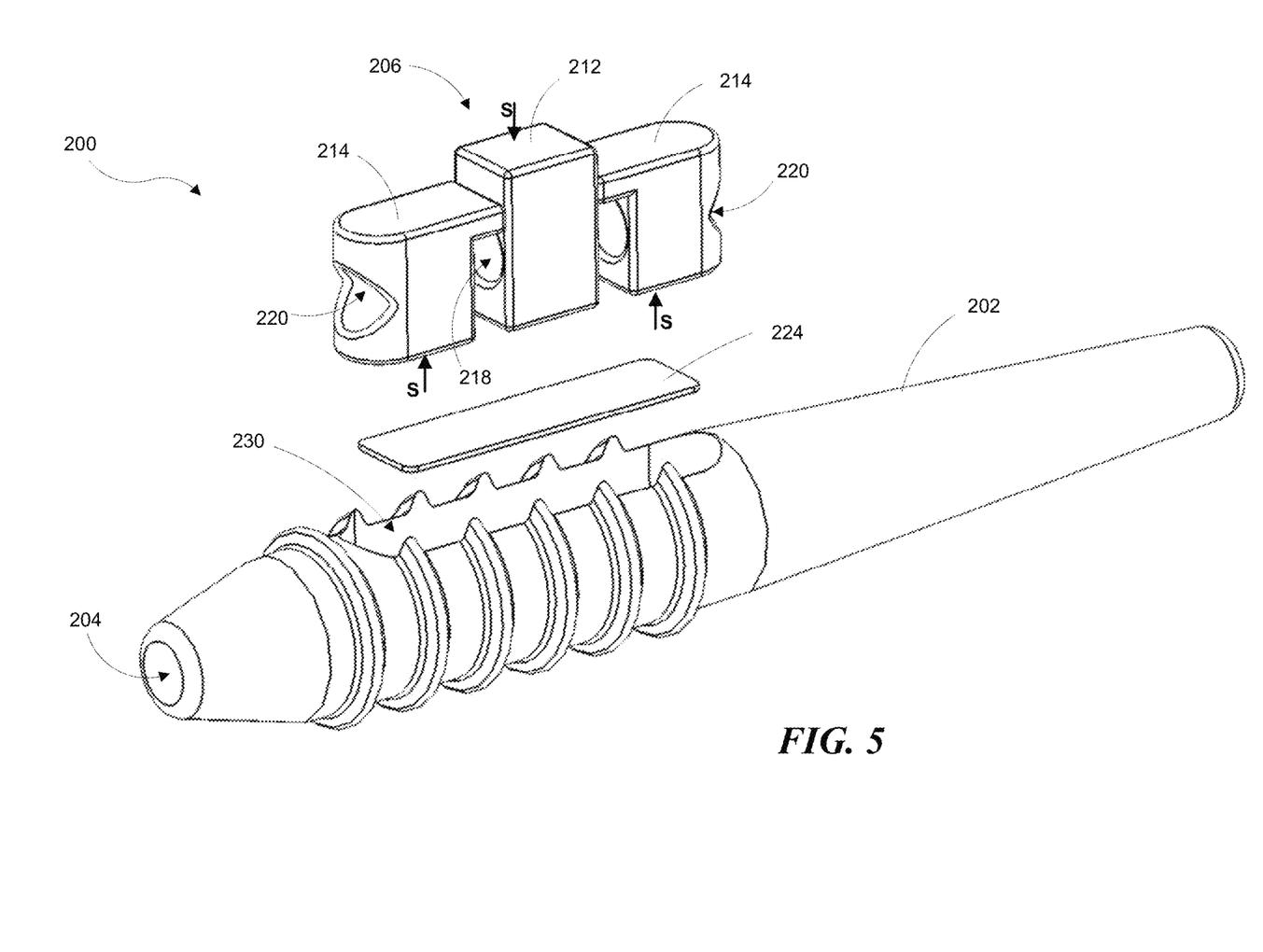
FIG. 5 is an exploded isometric view of the representative lead anchor shown in FIGS. 4A and 4B.

As shown in FIG. 5, the anchor body 202 can include a retainer pocket 230 positioned to intersect the lumen 204 and receive the retainer 206. The retainer 206 can comprise an inner grip block 212 having an inner aperture 218 and a pair of outer grip blocks 214 each having a corresponding outer aperture 220. The retainer 206 can include a leaf spring 224 connecting the inner grip block 212 with the outer grip blocks 214. The leaf spring 224 can be glued or mechanically fastened to the grip blocks 212, 214, for example. In some embodiments, the leaf spring 224 can comprise a flat strip of material providing a resilient or spring-like behavior. Accordingly, the leaf spring 224 may be comprised of a metal, such as for example and without limitation, titanium, Elgiloy®, spring steel, or the like. The grip blocks 212 and 214 can comprise plastic, such as, for example and without limitation, ABS, Nylon, Delrin, UHMW polyethylene, and the like.

The outer apertures 220 are generally coaxial with each other and aligned with the lumen 204 (see FIG. 4B). However, the inner aperture 218 is offset (e.g., upwardly) from the outer apertures 220 when the leaf spring 224 is in a relaxed state as shown in FIG. 4B, for example. The retainer 206 is normally in a relaxed or engaged state in which the lead is pinched between the inner and outer apertures. Thus, to insert the lead through the anchor body, or move the lead within the lumen 204, the retainer 206 is actuated (e.g., elastically deformed) to a disengaged state to release the compressive force on the lead. To actuate the retainer 206, a user can push the inner grip block 212 and the outer grip blocks 214 together (as indicated by arrows S) to align the inner and outer apertures 218 and 220, respectively. The user can push the inner grip block 212 and the outer grip blocks 214 together by manually squeezing the retainer 206 or by using a suitable tool, such as the lead anchor tool described below with reference to FIG. 8.

Figures 6A, 6B:
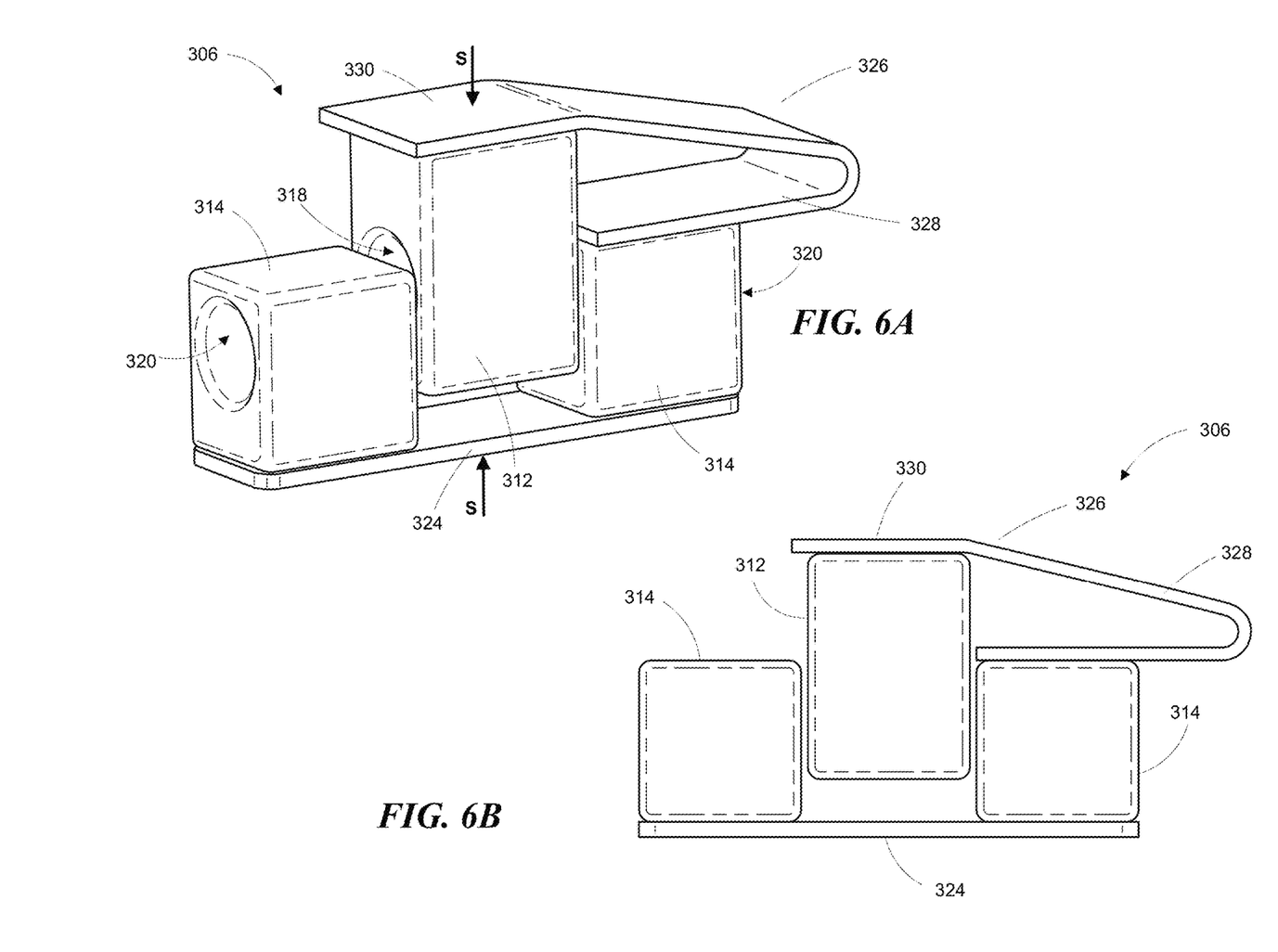
FIG. 6A is an isometric view of a lead anchor spring clip according to representative embodiments of the present technology.
FIG. 6B is a side view in elevation of the representative spring clip shown in FIG. 6A.

FIGS. 6A and 6B illustrate another lead anchor retainer 306 according to representative embodiments of the present technology. The retainer 306 can be positioned in a suitable anchor body, such as the anchor body 202 described above with respect to FIG. 5. The retainer 306 can comprise an inner grip block 312 having an inner aperture 318 and a pair of outer grip blocks 314, each having a corresponding outer aperture 320. The retainer 306 can include a connector plate 324 connecting the outer grip blocks 314 together. The connector plate 324 can be glued or mechanically fastened to the grip blocks 314, for example. A resilient member, such as spring 326, can connect to at least one of the outer grip blocks 314 and carries the inner grip block 312 therebetween such that the inner aperture 318 is offset from the outer apertures 320 when the spring 326 is in a relaxed state. In some embodiments, the spring 326 can comprise a U- or V-shaped portion 328 and a flat transverse portion 330. The U-shaped portion 328 is attached to the outer grip block 314 and the transverse portion 330 is attached to the inner grip block 312.

In some embodiments, the spring 326 can comprise a continuous strip of material bent (e.g., stamped) into the configuration shown and described herein. For example, the retainer 326 can comprise a material providing a resilient or spring-like behavior. Accordingly, the spring 326 may be comprised of a metal, such as for example and without limitation, titanium, Elgiloy®, spring steel, or the like. The grip blocks 312 and 314 can comprise plastic, such as, for example and without limitation, ABS, Nylon, Delrin, UHMW polyethylene, and the like.

The outer apertures 320 are generally coaxial with each other and aligned with a lumen of the anchor body. However, the inner aperture 318 is offset (e.g., upwardly) from the outer apertures 320 when the spring 326 is in a relaxed state as shown in FIGS. 6A and 6B, for example. The retainer 306 is normally in a relaxed or engaged state in which the lead is pinched between the inner and outer apertures. Thus, to insert the lead through the anchor body, or move the lead within the lumen, the retainer 306 is actuated (e.g., elastically deformed) to a disengaged state to release the compressive force on the lead. To actuate the retainer 306, a user can push the inner grip block 312 (e.g., downwardly relative to the outer grip blocks 314) to align the inner and outer apertures 318 and 320, respectively. The user can align the apertures 318, 320 by manually squeezing the retainer 306 (as indicated by arrows S) or by using a suitable tool, such as the lead anchor tool described below with reference to FIG. 8.

Figure 7:
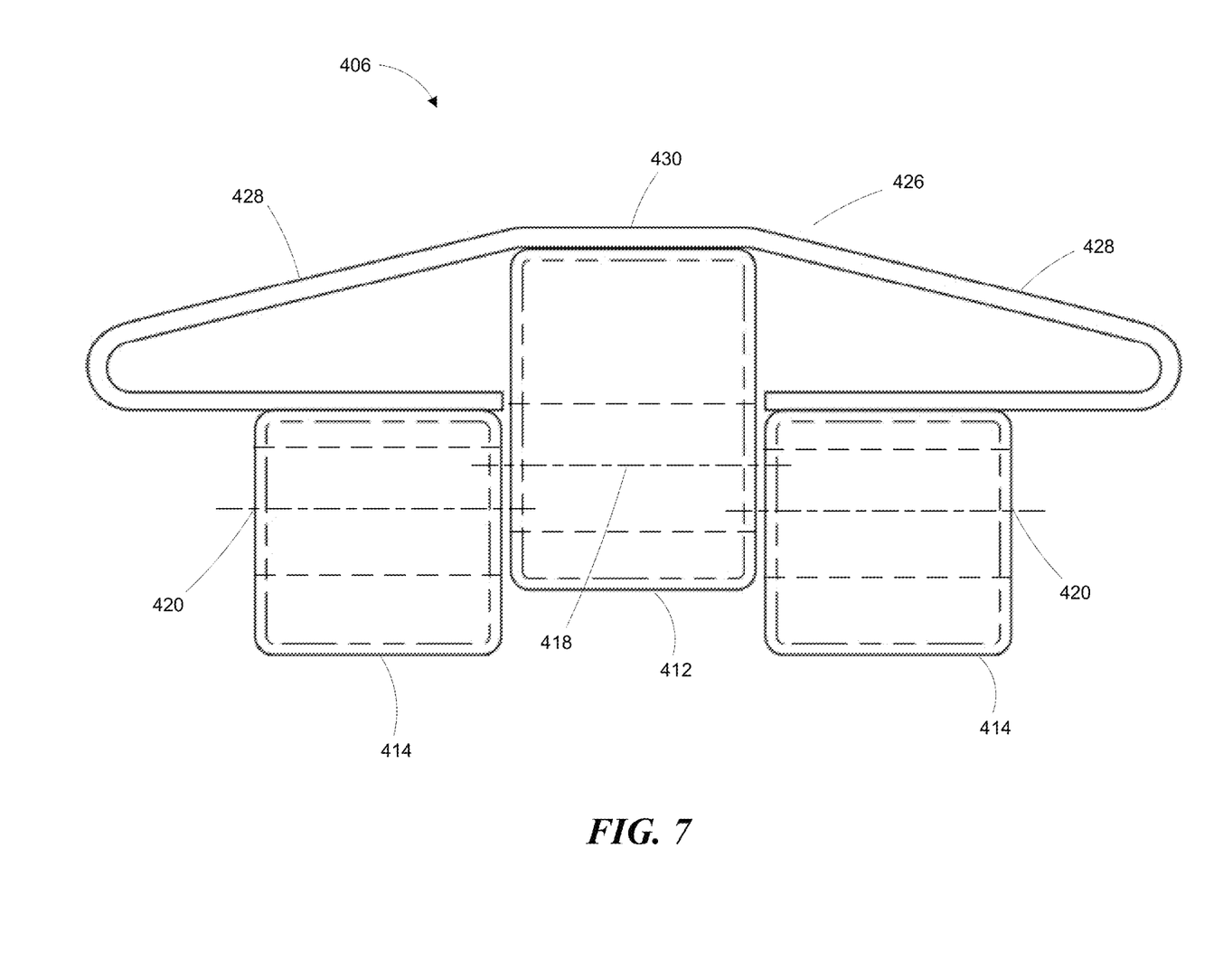
FIG. 7 is a side view in elevation of a lead anchor spring clip according to further representative embodiments of the present technology.

FIG. 7 illustrates a lead anchor retainer 406 according to further representative embodiments of the present technology that is generally similar to the lead anchor retainer 306 described with respect to FIGS. 6A and 6B. In this embodiment, a resilient member, such as spring 426, includes a pair of opposed U-shaped resilient portions 428 connected by a transverse portion 430. The U-shaped resilient portions 428 each connect to a corresponding outer grip block 414 and the transverse portion 430 carries the inner grip block 412 therebetween such that the inner aperture 418 is offset from the outer apertures 420 when the spring 426 is in a relaxed state. In some embodiments, the retainer 406 can also include a connector plate, such as the connector plate 324 (FIG. 6A), connecting the outer grip blocks 414 together.

Figure 8:
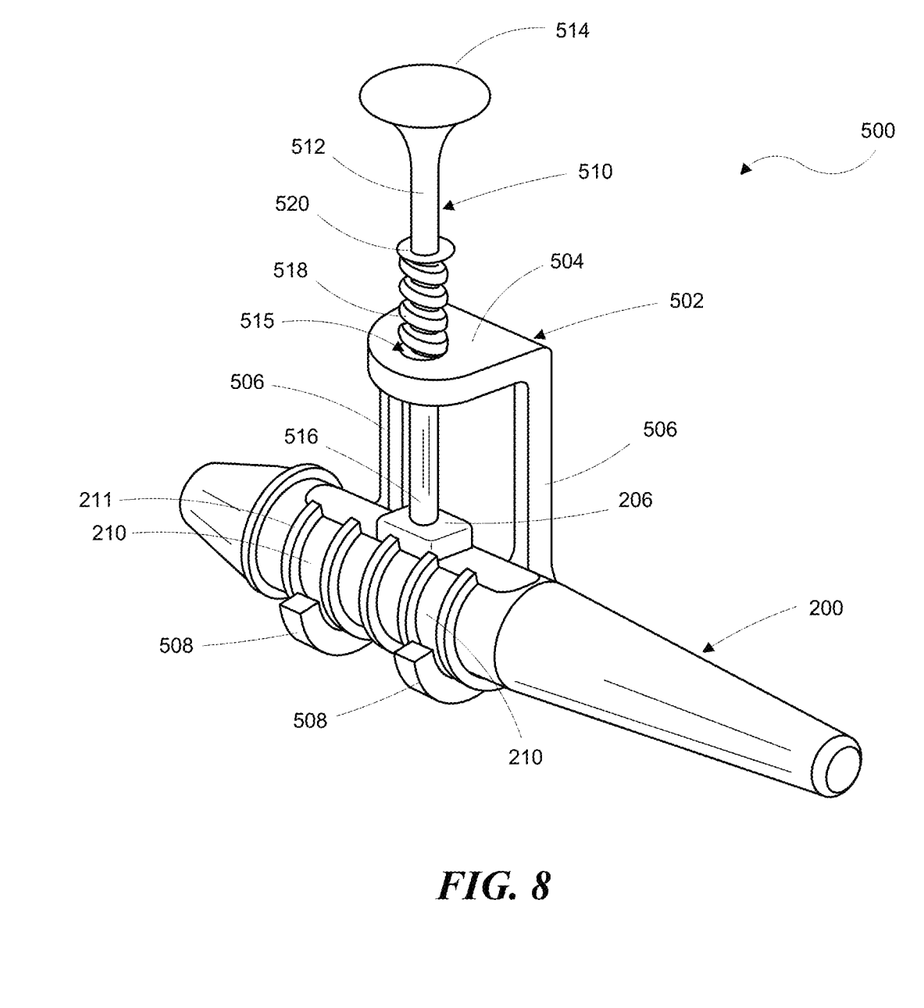
FIG. 8 is a perspective view of a lead anchor actuation tool according to representative embodiments of the present technology.

FIG. 8 illustrates a lead anchor actuation tool 500 according to representative embodiments of the present technology. The lead anchor tool 500 can comprise a frame 502 having a collar portion 504 and a pair of anchor support arms 506 extending from the collar portion 504. Each anchor support arm 506 can include a finger portion 508 extending transversely from the support arm 506. In some embodiments, the finger portions 508 can be at least partially arcuate, as shown in FIG. 8. A moveable plunger 510 is carried by the collar portion 504. The plunger 510 is slidable in an aperture 515 formed through the collar portion 504. The plunger 510 can include an elongate plunger rod 512 having a proximal end portion 514 and a distal end portion 516. A resilient member, such as compression spring 518 is positioned around a portion of the plunger 510 to urge the distal end portion 516 away from the finger portions 508. In some embodiments, the proximal end portion 514 includes or is in the form of a push knob. The compression spring 518 can be positioned around the plunger rod 512 between the collar portion 504 and a spring retainer, such as a washer or a circlip 520, secured to the plunger rod 512. The plunger 510 can be moveably retained relative to the collar portion 504 by a rod retainer (not visible) attached to the plunger rod 512 under the collar portion 504, or the distal end portion 516 can have a diameter larger than that of the aperture 515. Accordingly, the plunger 510 has a limited range of axial motion and is "captured" by the collar portion 504.

In another embodiment, the plunger rod 512 can include a threaded portion that mates with a threaded hole in the collar portion 504, whereby turning the knob 514 in a clockwise direction causes the distal end portion 516 to move toward the finger portions 508 and turning the knob 514 in a counter-clockwise direction causes the distal end portion 516 to move away from the finger portions 508.

In operation, the finger portions 508 are positionable against a side of a lead anchor, such as the lead anchor 200, and the distal end portion 516 of the plunger rod 512 is positionable against a retainer of the lead anchor 200, such as the retainer 206. A user can grasp the tool 500 with a forefinger positioned under the collar portion 504 and a thumb positioned on the knob 514. The user can then actuate the retainer 206 by pressing the knob 514 with his/her thumb. Pressing the knob 514 causes the distal end portion 516 to press on the retainer 206, thereby aligning the retainer apertures to allow insertion or movement of a lead therethrough. Once the user releases the knob 514, the spring 518 moves the distal end portion 516 away from the retainer 206, so that the retainer engages the lead as described herein. The tool can then be removed from the lead anchor 200. Although the figure appears to show the anchor actuation tool 500 with finger portions 508 positioned in the suture grooves 210 of the anchor 200, other surfaces can be pressed together to actuate the retainer 206. For example, a different type of tool could alternatively engage the raised ribbed portions 211. In a preferred embodiment, two flat surfaces (e.g., forceps or similar tool) can be used to press the raised rib portions 211 and the raised surface of retainer 206 together to squeeze the anchor.

Figure 9A:
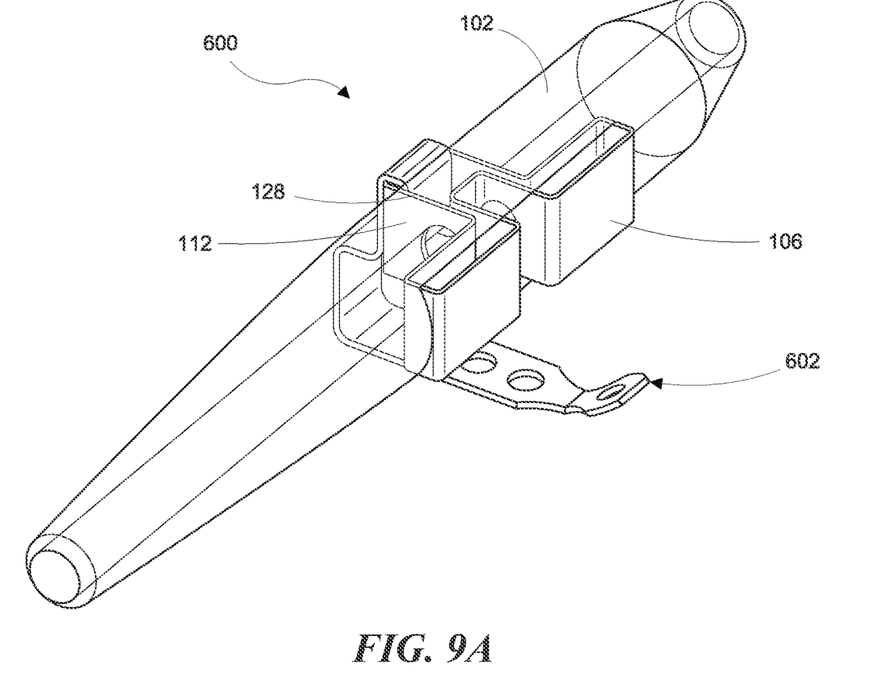
FIG. 9A is an isometric view of a lead anchor according to representative embodiments of the present technology.
Figure 9B:
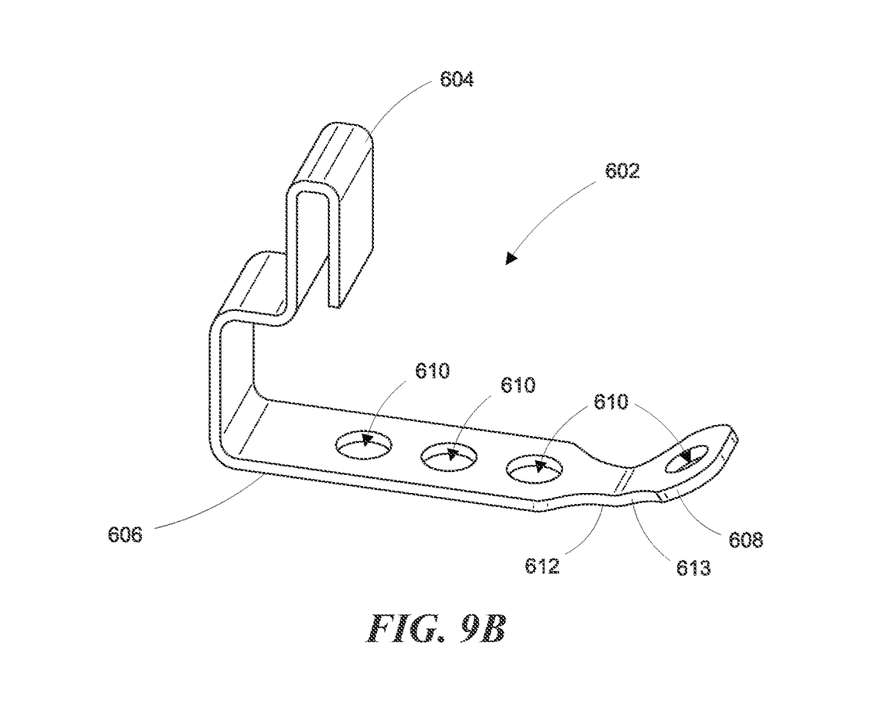
FIG. 9B is an isometric view of the representative retention tab shown in FIG. 9A.

FIGS. 9A and 9B illustrate another lead anchor 600 according to representative embodiments of the present technology. The lead anchor 600 is similar to the lead anchor 100 described above with respect to FIGS. 1A and 1B. For example, the lead anchor 600 can include the same or a similar longitudinally extending anchor body 102 and retainer 106, with the addition of a retention tab 602. The retention tab 602 can be attached to the outer grip member 112 of the retainer 106. For example, a clip portion 604 (FIG. 9B) of the retention tab 602 can engage the transverse tabs 128 (see FIG. 2A). In some embodiments, the clip portion 604 can be welded to the transverse tabs 128 (e.g., spot welded).

With continued reference to FIG. 9B, the retention tab 602 can include an arm portion 606 extending from the clip portion 604. The arm portion 606 can carry an angled tip portion 608. In some embodiments, the tip portion 608 is angled toward the retainer 106 (i.e., upward in the present figures) to help control tissue depth and ergonomics. The tip portion 608 can be rounded or blunt in order to facilitate moving and maneuvering the retention tab 602 through a patient's fascia. In some embodiments, the arm portion 606 includes a narrow section 612 to increase engagement with the fascia by providing increased area around the perimeter 613 of the tip portion 608 to help prevent unintended movement against the fascia. The arm portion 606 and the tip portion 608 can include suture holes 610 to facilitate suturing the retention tab 602 to the patient. In some embodiments, the retention tab 602 can comprise a ductile material such that it can bend and lock the lead anchor 600 in position. In some embodiments, narrow sections, such as section 612, can be positioned along the arm portion 606 to tailor where it is intended to more easily bend.

Figure 10A:
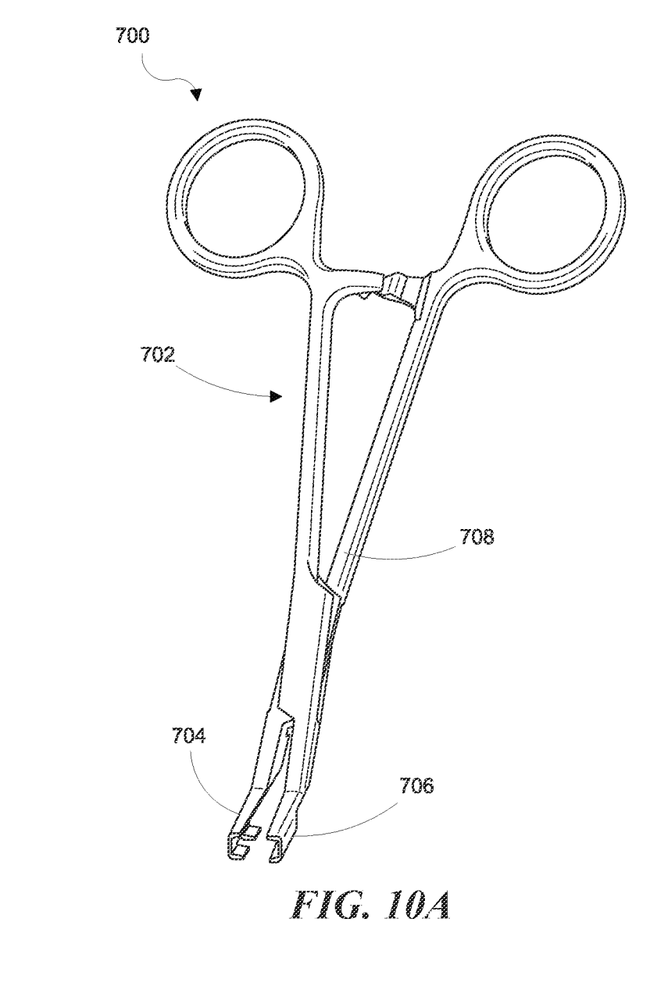
FIG. 10A is an isometric view of a lead anchor actuation tool according to representative embodiments of the present technology.
Figure 10B:
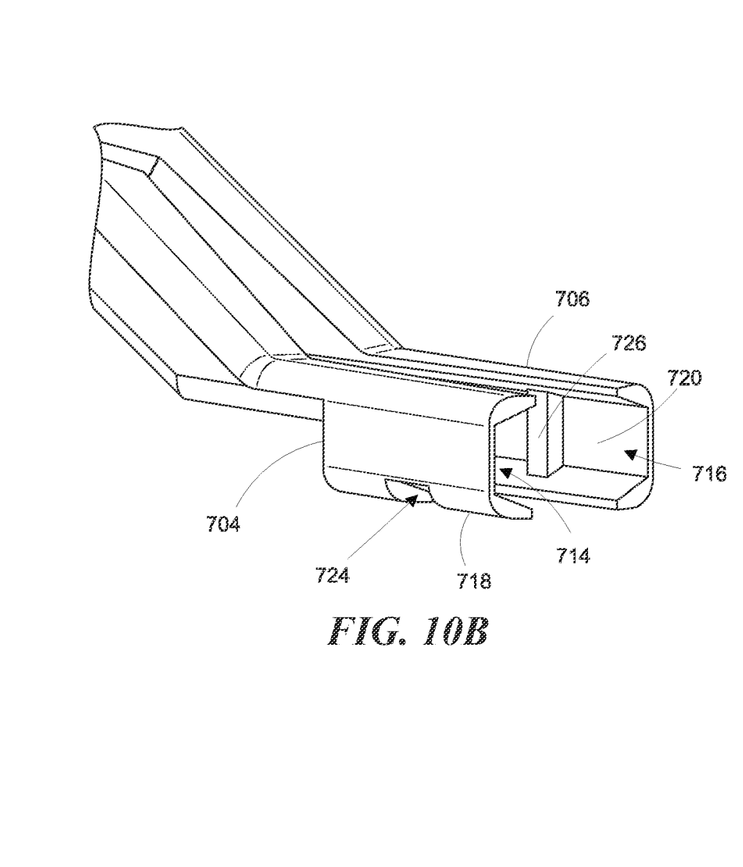
FIG. 10B is an enlarged partial isometric view of the actuation tool shown in FIG. 10A.

FIGS. 10A and 10B illustrate a lead anchor actuation tool 700 according to representative embodiments of the present technology. The lead anchor tool 700 can comprise a hemostat 702 having first and second jaw portions 704 and 706 each of which can be angled with respect to the handles 708. Referring to FIG. 10B, each jaw portion 704 and 706 can comprise a channel 714 and 716, respectively. The first jaw portion 704 can include a notch 724 positioned in the lower flange 718 of channel 714 to receive the arm portion 606 of the retention tab 602 (see FIGS. 9A and 9B). The second jaw portion 706 can include a transverse rib 726 positioned on the web 720 inside the channel 716. The rib 726 is positioned to engage the inner member 114 of the retainer 106 (see FIG. 2) ensuring consistent orientation of the anchor and optimizing stability/control of the anchor during placement.

Figure 11A:
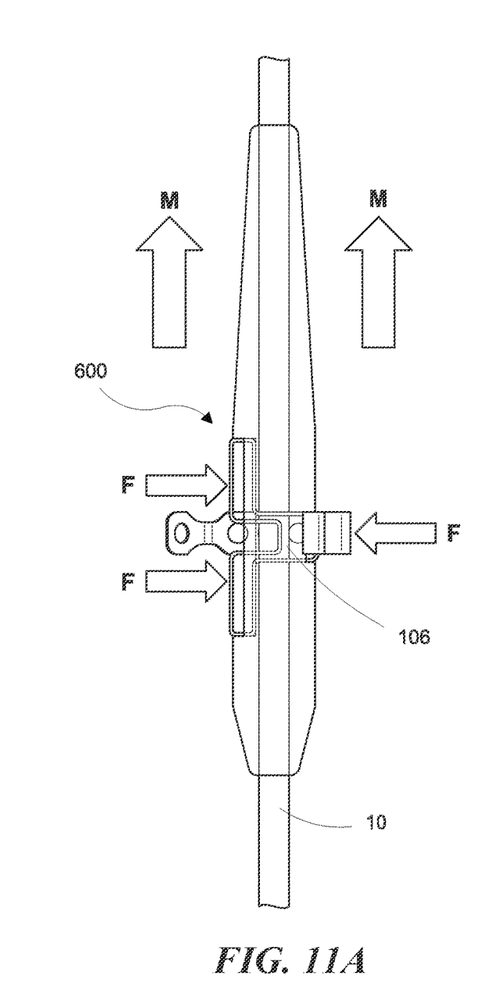
FIG. 11A is a top view of the lead anchor shown in FIGS. 9A and 9B.
Figure 11B:
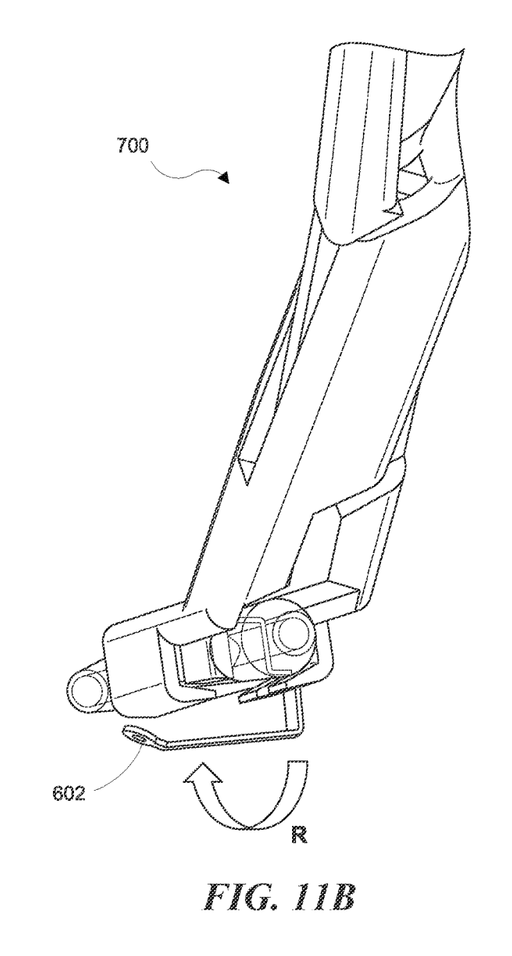
FIG. 11B is an enlarged partial isometric view of the actuation tool shown in FIGS. 10A and 10B illustrating insertion of the lead anchor.

As illustrated in FIGS. 11A and 11B, the lead anchor actuation tool 700 can be used to squeeze the retainer 106 as indicated by arrows F to disengage the retainer 106 allowing the anchor 600 to be moved along the lead 10 as indicated by arrows M. The lead anchor actuation tool 700 can be used to maneuver the retention tab 602 into the patient's fascia with a rotating motion indicated by arrow R. Once the anchor 600 is in position, the retention tab 602 can be deformed (e.g., bent in the direction of arrow R) to lock the anchor in position.

The present technology also includes methods of anchoring a lead to a patient using a lead anchor. A representative method comprises moving a retainer disposed in an anchor body to a disengaged state; inserting a lead into the anchor body while the retainer is in the disengaged state; and relaxing the retainer to an engaged state. The method can further comprise placing the retainer in the disengaged state and repositioning the lead with respect to the anchor body. The method can comprise actuating the retainer manually or by using a suitable tool. The method can further comprise attaching the anchor body to a patient. In some embodiments, moving the retainer to a disengaged state can include aligning inner and outer apertures of the retainer.

Several embodiments described herein offer advantages over traditional lead anchors. For example, certain embodiments include a retainer that retains the lead in position with fewer parts than traditional lead anchors have. Accordingly, the disclosed lead anchors can be smaller than traditional lead anchors, which results in a device that is more comfortable for the patient. With fewer parts, the lead anchor can be more economical to produce when compared to traditional lead anchors having additional parts. The disclosed lead anchors are also easy to use. Via a simple manual squeezing operation, or via one movement of a suitable tool, the retainer may be engaged or disengaged in order to position, reposition, or secure a lead within the lead anchor body.

The present technology includes lead anchors for use with neurological stimulation systems, such as spinal cord modulation systems. In representative embodiments, the lead anchor comprises a longitudinally extending anchor body and a retainer. The anchor body can include a lumen positioned to receive a spinal cord lead therethrough and a retainer pocket intersecting the lumen. The retainer is positioned in the retainer pocket and includes a first grip member, having at least one first aperture, and a second grip member, having at least one second aperture. At least one spring portion (e.g., having a U-shape) connects the first and second grip members.

In one aspect of the disclosed technology, the at least one first aperture is generally aligned with the lumen. In another aspect of the disclosed technology, the at least one second aperture is offset from the first aperture when the at least one spring portion is in a relaxed state. In yet another aspect of the disclosed technology, the first grip member comprises a pair of opposed first wall portions and a pair of generally coaxial first apertures, each formed through a corresponding one of the pair of opposed first wall portions. In one aspect of the disclosed technology, the second grip member comprises a pair of opposed second wall portions and a pair of generally coaxial second apertures, each formed through a corresponding one of the pair of opposed second wall portions, wherein the second grip member is positioned between the pair of opposed first wall portions. In a further aspect of the disclosed technology, the at least one U-shaped spring portion comprises two U-shaped spring portions, each positioned on opposite sides of the pair of opposed first wall portions. In one aspect of the disclosed technology, the retainer comprises a continuous strip of material. In another aspect of the disclosed technology, the retainer pocket includes a central region intersecting the lumen and a pair of lateral ledge regions, each at least partially containing a corresponding one of the U-shaped spring portions.

In another representative embodiment, the lead anchor comprises a longitudinally extending anchor body and a retainer. The anchor body can include a lumen positioned to receive a spinal cord lead therethrough and a retainer pocket intersecting the lumen. The retainer is positioned in the retainer pocket and includes an inner grip block, having an inner aperture, and at least one outer grip block, having an outer aperture. A spring connects the inner and outer grip blocks.

In one aspect of the disclosed technology, the outer aperture is generally aligned with the lumen. In another aspect of the disclosed technology, the inner aperture is offset from the outer aperture when the spring is in a relaxed state. In yet another aspect of the disclosed technology, the at least one outer grip block comprises a pair of outer grip blocks and a pair of generally coaxial outer apertures, each formed through a corresponding one of the pair of outer grip blocks. In a further aspect of the disclosed technology, the lead anchor can include a connector plate positioned opposite the spring for joining the outer grip blocks. In one aspect of the disclosed technology, the spring connects to both of the outer grip blocks and carries the inner grip block therebetween such that the inner aperture is offset from the outer apertures when the spring is in a relaxed state. In another aspect of the disclosed technology, the spring includes a pair of opposed U-shaped spring portions, each connected to a corresponding one of the outer grip blocks.

The present technology includes tools for actuating lead anchors. In a representative embodiment, the lead anchor tool comprises a frame, a movable plunger carried by the frame, and a resilient member. The frame can include a collar portion and at least one anchor support arm extending from the collar portion. The anchor support arm can include a finger portion extending transversely from the support arm. The moveable plunger is carried by the collar portion. The plunger can include an elongate plunger rod having a proximal end portion and a distal end portion. The resilient member is positioned to urge the distal end portion of the plunger away from the finger portion.

In one aspect of the disclosed technology, the finger portion is positionable against a side of a lead anchor and the distal end portion is positionable against a retainer of the lead anchor. In another aspect of the disclosed technology, the proximal end portion includes a push knob. In yet another aspect of the disclosed technology, the resilient member comprises a compression spring positioned along the plunger rod between the collar portion and a retainer secured to the plunger rod. In a further aspect of the disclosed technology, the at least one anchor support arm comprises two anchor support arms.

From the foregoing, it will be appreciated that specific embodiments of the disclosed technology have been described herein for purposes of illustration, but that various modifications may be made without deviating from the technology. Certain aspects of the disclosure described in the context of particular embodiments may be combined or eliminated in other embodiments. Further, while advantages associated with certain embodiments have been described in the context of those embodiments, other embodiments may also exhibit such advantages, and not all embodiments need necessarily exhibit such advantages to fall within the scope of the present disclosure. Accordingly, the present disclosure and associated technology can encompass other embodiments not expressly shown or described herein.

REMARKS

The above description and drawings are illustrative and are not to be construed as limiting. Numerous specific details are described to provide a thorough understanding of the disclosure. However, in some instances, well-known details are not described in order to avoid obscuring the description. Further, various modifications may be made without deviating from the scope of the embodiments.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not for other embodiments.

The terms used in this specification generally have their ordinary meanings in the art, within the context of the disclosure, and in the specific context where each term is used. It will be appreciated that the same thing can be said in more than one way. Consequently, alternative language and synonyms may be used for any one or more of the terms discussed herein, and any special significance is not to be placed upon whether or not a term is elaborated or discussed herein. Synonyms for some terms are provided. A recital of one or more synonyms does not exclude the use of other synonyms. The use of examples anywhere in this specification, including examples of any term discussed herein, is illustrative only and is not intended to further limit the scope and meaning of the disclosure or of any exemplified term. Likewise, the disclosure is not limited to various embodiments given in this specification. Unless otherwise defined, all technical and scientific terms used herein have the same meaning as commonly understood by one of ordinary skill in the art to which this disclosure pertains. In the case of conflict, the present document, including definitions, will control.

What is claimed is:

1. A lead anchor, comprising:
   a longitudinally extending anchor body having a lumen extending entirely through the anchor body and positioned to receive a spinal cord lead therethrough, and having a retainer pocket intersecting the lumen; and
   a retainer positioned in the retainer pocket, the retainer comprising:
   a first grip member having at least one first aperture;
   a second grip member having at least one second aperture; and
   a U-shaped resilient portion connecting the first and second grip members.

2. The lead anchor of claim 1, wherein the at least one first aperture is generally aligned with the lumen.

3. The lead anchor of claim 2, wherein the at least one second aperture is offset from the first aperture when the at least one U-shaped resilient portion is in a relaxed state.

4. The lead anchor of claim 1, wherein the first grip member comprises a pair of opposed first wall portions and a pair of generally coaxial first apertures, each formed through a corresponding one of the pair of opposed first wall portions.

5. The lead anchor of claim 4, wherein the second grip member comprises a pair of opposed second wall portions and a pair of generally coaxial second apertures, each formed through a corresponding one of the pair of opposed second wall portions, wherein the second grip member is positioned between the pair of opposed first wall portions.

6. The lead anchor of claim 5, wherein the U-shaped resilient portion is a first U-shaped resilient portion and wherein the lead anchor further comprises a second U-shaped resilient portion, each of the first and second U-shaped resilient portions being positioned on opposite sides of the pair of opposed first wall portions.

7. The lead anchor of claim 6, wherein the retainer comprises a continuous strip of material.

8. The lead anchor of claim 6, wherein the retainer pocket includes a central region intersecting the lumen and a pair of lateral ledge regions, each at least partially containing a corresponding one of the first and second U-shaped resilient portions.

* * * * *